(12) United States Patent
Jurgens et al.

(10) Patent No.: US 6,472,502 B1
(45) Date of Patent: Oct. 29, 2002

(54) ABSORBABLE COPOLYLACTIDES AND THEIR USE

(76) Inventors: Christian Jurgens, c/o Merck KGaA, 64271 Darmstadt (DE); Hans Rytger-Kricheldorf, c/o Merck KGaA, 64271 Darmstadt (DE); Ingrid Kreiser-Saunders, c/o Merck KGaA, 64271 Darmstadt (DE)

( * ) Notice: Subject to any disclaimer, the term of this patent is extended or adjusted under 35 U.S.C. 154(b) by 0 days.

(21) Appl. No.: 09/641,334

(22) Filed: Aug. 18, 2000

(30) Foreign Application Priority Data

Aug. 18, 1999 (EP) .............................. 99116119

(51) Int. Cl.⁷ .............................. C08G 63/08
(52) U.S. Cl. ................ 528/354; 528/485; 528/495; 528/501; 528/503
(58) Field of Search ............... 528/354, 485, 528/495, 501, 503

(56) References Cited

U.S. PATENT DOCUMENTS 3,755,558 A    8/1973   Scribner
4,045,418 A    8/1977   Sinclair
5,466,444 A    11/1995  Juergens et al.

FOREIGN PATENT DOCUMENTS

EP   509 203    2/1992
FR   2126270    2/1972

*Primary Examiner*—Duc Truong
(74) *Attorney, Agent, or Firm*—Millen, White, Zelano & Branigan, P.C.

(57) ABSTRACT

The invention relates to novel copolylactides which have been polymerized from units of racemic lactide and the comonomers ε-caprolactone, δ-valerolactone, 1,4-dioxan-2-one or 1,3-dioxan-2-one in a lactide/comonomer molar ratio of 90–80/10–20 in the presence of tin(II) di(ethylhexanoate) as initiator and of a cocatalyst at about 160° C., and have a glass transition temperature between 30 and 43° C., a molecular weight $M_n$ of from 15,000 to 50,000 and a polydispersity $P_n$ ($M_w/M_n$) between 1.2 and 2. The novel copolylactides are particularly suitable in an outstanding manner for the management of all types of wounds.

23 Claims, No Drawings

ABSORBABLE COPOLYLACTIDES AND THEIR USE

The invention relates to novel copolylactides which have been polymerized from units of racemic lactide and the comonomers ε-caprolactone, δ-valerolactone, 1,4-dioxan-2-one or 1,3-dioxan-2-one in a lactide/comonomer molar ratio of about 90–80/10–20 in the presence of tin(II) di(ethylhexanoate) as initiator and of a cocatalyst at about 160° C., and have a glass transition temperature between about 30 and 43° C., a molecular weight $M_n$ of about 15,000 to 50,000 and a polydispersity $P_n$ ($M_2/M_n$) of about 1.2 to 2. The novel copolylactides are particularly suitable in an outstanding manner for the management of all types of wounds.

BACKGROUND OF THE INVENTION

U.S. Pat. No. 4,045,418 describes a copolymer consisting of D,L-lactide and ε-caprolactone in the presence of tin(II) caprylate as initiator. The copolymer is transparent, rigid and brittle and is used as a disposable product and molding in the automobile industry, in the home and in the packaging industry. The molecular weights are between 100,000 and 300,000. These copolymers are unsuitable in dissolved form for medical applications, for example as surgical incise drapes or a sliquid gloves because, after spraying onto the skin, they cure as a film, with evaporation of the solvent, and therefore become brittle and crazed.

FR-2126270 discloses film-forming polymers of lactic acid and glycolic acid in solvents such as, for example, ethyl acetate, which additionally comprise pharmacological active ingredients and can be employed, for example, as spray dressings.

A disadvantage of these polylactones is the fact that they are suitable only as active ingredient carriers on intact skin because the polymer/drug mixture is always applied as solution to the skin. However, chloroform, difluorodichloromethane or ethyl acetate which are used as solvents would seriously harm an open wound.

EP-B1-270,987 describes a process for preparing catalyst-free absorbable homopolymers or copolymers based on hydroxy acids. Lactide and glycolide are mainly employed for copolymer formation. However, glycolide is unsuitable for obtaining copolymers for the desired topical application because glycolide copolymers are degraded too quickly.

EP-0 509,203 relates to the use of copolymers of racemic lactide and ε-caprolactone, δ-valerolactone, γ-decalactone or β-hydroxybutyric acid, prepared by reacting the monomers in a molar ratio of lactide to reactant of about 95–70:5–30 with the addition of tin(II) di(ethylhexanoate) initiator at temperatures of about 150° C. over a period of 16 to 48 hours, for the topical treatment of human or animal skin. The said earlier property right of the applicant then states further that the copolymers most suitable for topical applications have a molar ratio of initiator to reactant of about 1:100 to 1:500. To remove remaining monomers, short-chain oligomers or, if appropriate, also excess plasticizers, the reaction composition is usually precipitated with 600–800 times the amount of alcohol. It is true that the copolymers obtained as disclosed in EP 0509203 show properties which are more suitable for topical wound treatment than the polymer products of U.S. Pat. No. 4,045,418. However, they still do not have optimal characteristics in respect of flexibility, adhesiveness, avoidance of tackiness etc. In addition, complying with the preparation conditions disclosed frequently results in products with non-reproducible and occasionally unusable properties.

SUMMARY OF THE INVENTION

The teaching of the present invention is based on the object of further improving in a plurality of ways absorbable, physiologically acceptable copolylactides of the type described. An important fact in this connection is that application to uninjured skin requires copolylactides with high adherence, flexibility and stretchability. The permeability to water vapor is of less importance here than for application to wounds, and the degradation may also take place somewhat faster but ought not to take less than 24 hours for a film thickness of about 3–5 μm even in an aqueous medium. Impermeability to hydrophilic and lipophilic allergens is a requirement. Accordingly, amorphous copolylactides, although with low viscosity (=short-chain polymers), are to be preferred for these applications too. The permeability to water vapor is a crucial criterion for use on injured skin and cannot be achieved solely by the copolymers because they are hydrophobic and of low permeability (<60 ml/h/m$^2$). The need in this case is either for a relatively high monomer content in the reaction product or else for the addition of hygroscopic/hydrophilic substances (for example glycerol), resulting in a vapor permeability initially at high levels (>150 ml/h/m$^2$), which decreases over the course of days (in accordance with the wound discharge).

Impermeability to microbes with a film thickness of 25–50 μm for a period of at least 14 days is a requirement. This can be achieved only by relatively long molecule chains (=higher viscosity).

It is furthermore important that the copolymers intended for the predefined purpose of use do not have a tacky consistency. This object is now achieved by the copolylactides according to the invention.

The invention thus relates to a flexible, transparent copolylactide which is composed of polymerized units of racemic lactide and the comonomers ε-caprolactone, δ-valerolactone, 1,4-dioxan-2-one or 1,3-dioxan-2-one and has a glass transition temperature ($T_g$) between 30 and 43° C., a number average molecular weight $M_n$ of from 15,000 to 50,000 and a molecular weight distribution (polydispersity $P_n$) of from 1.2 to 2. A consequence of this is that the weight average molecular weight $M_w$ of the copolylactide has a value of distinctly less than 100,000.

The properties of these copolylactides according to the invention differ distinctly from those in U.S. Pat. No. 4,045,418 and EP 0509 203, as is evident from the table below and is explained hereinafter. Thus, as has been shown in comparative examples, the glass transition temperature, for example, of the copolymers of EP 0509 203 is distinctly below 30° C., whereas it is over 45° C. for the products of U.S. Pat. No. 4,045,418.

Particularly advantageous copolylactides which are preferred for the purpose of the invention have a glass transition temperature of from 30 to 40° C., in particular 33 to 37° C., and a number average molecular weight $M_n$ of from 25,000 to 40,000, with a polydispersity of from 1.4 to 1.7. These particularly preferred properties are possessed in particular by copolylactides comprising ε-caprolactone as comonomeric unit. However, surprisingly, δ-valerolactone, 1,4-dioxan-2-one or 1,3-dioxan-2-one are also suitable according to the invention, as are mixtures of the individual comonomers, whereby it is possible where appropriate to achieve fine adjustment of the required properties.

As for virtually every polymeric compound, the properties of the copolylactides according to the invention depend on the conditions and parameters in the process for their preparation.

The invention thus also relates to a process for preparing a corresponding copolylactide, in which a racemic lactide is reacted with a comonomer selected from ε-caprolactone, δ-valerolactone, 1,4-dioxan-2-one or 1,3-dioxan-2-one or mixtures thereof. The molar ratio of lactide to comonomer in this process is 90–80:10–20. Particularly preferred lactide/comonomer ratios are 84:16, 85:15 or 86:14.

It is preferred for the polymerization of the monomeric units to give the copolymers with the required properties to use tin(II) di(ethylhexanoate) as initiator and a cocatalyst for accurate control of the polymerization process.

In order to obtain particularly good results, it is preferable for the initiator to be purified immediately before the polymerization reaction. Since the purchased initiator (tin(II) di(ethylhexanoate)) may contain up to 20% impurities in the form of water and free octanoic acid, these are preferably removed. The liquid initiator can, for example, be mixed with xylene (low-cost, nontoxic) or alternatively with toluene and subjected to azeotropic distillation one or more times. Subsequent fractional distillation under high vacuum (about $10^{-3}$ mbar) is advisable. Other purification processes which lead to substantial removal of the said impurities are likewise possible.

The molar ratio of initiator to lactide/comonomer employed in the process according to the invention is preferably about 1:30,000 to 1:50,000; a ratio of about 1:40,000 (±5% is more preferably used. Increasing this ratio causes the proportion of longer molecule chains to increase and thus also the softening point to increase in an undesired manner. EP 509,203 discloses, by contrast, a ratio of initiator to lactide/monomer of from 1:100 to 1:500. The present invention thus not only has an effect on the characteristics of the copolymer as such, but also entails the advantage that the amount of toxic tin initiator can be reduced by a factor of about 1000 (based on the molar ratio).

It is preferable also to use cocatalysts for accurate control of the chain lengths. Preferred cocatalysts which should be mentioned in particular are alkanols preferably with up to 18 C atoms, e.g., primary, secondary or tertiary alcohols, as well as polyols of corresponding alkanes. Also useable are oligoethylene glycol monomethyl ethers or polyols or mixtures of these. Particular preference is given to n-alkanols, especially n-butanol.

The molar ratio of cocatlyst to lactide/comonomer according to the invention is preferably about 1:200 to 1:600, more preferably 1:300 to 1:500. It has emerged that the cocatalyst used in this way plays an important part in the molecular weight distribution. The attempt, disclosed in EP 509,203, to remove short-chain copolymers by using alcohol to wash them out in relatively large amounts from the polymeric final product is thus unnecessary.

If required, it is possible to add plasticizers to the reaction mixture in order to alter the glass transition temperature and the vapor permeability. Examples of plasticizers used are glycerol, phthalic esters, tributyl citrate or excess caprolactone. The proportion of plasticizers should normally not exceed 10 to 20% by weight.

The polymerization of racemic lactide and of the comonomeric compound(s) takes place at a temperature not exceeding about 165° C. In one process variant, polymerization is carried out in one temperature step at a temperature between from 155 and 165° C., preferably about 150° C., in a period of from 40 to 55 h, preferably 46 to 50 h, in particular about 48 h. A preferred process variant uses a two-stage polymerization step: thus, polymerization is carried out initially at a temperature of from 155 to 165° C., preferably about 160° C., in a period of from 20 to 28 h, preferably about 24 h, and then at a temperature of from 90 to 120° C., preferably about 100° C., in a period of a further 20 to 28 h, preferably about 24 h. The choice and sequence of the temperatures and the duration of the polymerization depend in the final analysis on the required properties of the polymer.

After completion of the polymerization, the product is subjected in one embodiment to an evacuation process which serves to remove volatile substances from the polymerization mixture. Depending on the vacuum, this step takes according to the invention from 10 to 80, preferably from 40 to 60, minutes. The vacuum is applied at temperatures between room temperature and, preferably, 50 to 120° C., in particular 100° C.

As already mentioned above, it is possible by the process according to the invention to adjust and control the molecular weight of the copolymer, in particular the $M_w/M_n$ ratio which, in the final analysis, partly determines the required properties, in a more exact manner than hitherto possible in the state of the art for products of this type. The present invention thus also relates to a process for controlling the $M_w/M_n$ ratio, e.g., with a range of 1.2 to 2.0, preferably 1.4 to 1.7, in the preparation of a copolylactide comprising polymerized units of racemic lactide and the comonomers ε-caprolactone, δ-valerolactone, 1,4-dioxan-2-one or 1,3-dioxan-2-one, in which the process steps indicated above and in the claims are applied. The copolylactides according to the invention can, after cooling or while still a hot polymer, be rolled out without further addition to films (e.g., 10 to 100 μm thick) and can thus be employed for diverse medical and cosmetic purposes. The main area of use is the use as surgical incise drape, in particular for covering wounds.

Alternatively, the copolylactides according to the invention can also be dissolved in suitable solvents such as, for example, ethyl acetate, acetone or methylene chloride and be mixed with known disinfectants and/or with local anaesthetics. Ethyl acetate is preferably employed as solvent because it already has a disinfectant action.

The copolylactides can furthermore be employed particularly beneficially as liquid glove for handling allergens. They are thus a genuine alternative for example also for sufferers from allergies to dishwashing agents or detergents.

On use as sunscreens, conventional UVA and UVB filters are admixed with the complete solution.

The copolylactides according to the invention can also be employed as absorbable adhesives if they are dissolved in solvents suitable for this purpose (for example ethyl acetate).

In order to show that the copolymers of the state of the art, in particular of the disclosures in U.S. Pat. No. 4,045,410 and EP 0509 203, have different properties and thus differ substantially from those of the invention, the processes indicated therein for preparing them have been carried out in comparative tests according to the invention, and the resulting products have been compared with the those of the present invention. For this purpose, the same parameters and properties were measured in all the tests, which was the only way to make direct comparison possible.

In the following table, the properties of a copolymer according to the invention (Example 2) are shown with a copolymer according to U.S. Pat. No. 4,045,418 (Example 3 therein) and a copolymer according to EP-509 203 (Example 1 therein).

| Measured parameter | Invention | U.S. Pat. No. 4,045,418 | EP 0509 203 |
|---|---|---|---|
| Lactide/ε-caprolactone | 85/15 | 85/15 | 85/15 |
| $T_g$ (° C.) | 37 | 49 | 22 |
| Viscosity $\eta_{inh}$ (dl/g) | 0.6 | 1.6 | 0.31 |
| Mol. weight $M_w$ | 48,000 | 214,300 | 38,300 |
| Mol. weight $M_n$ | 30,000 | 34,600 | 17,410 |
| $M_w/M_n$ ratio | 1.6 | 6.2 | 2.2 |
| Behaviour as film on the skin at 37° | Good transparency, slow hydrolysis, adhesively flexible, contour following | Low flexibility, rigidly brittle, poor adhesion | Tacky, moderate transparency, rapid clouding of the film |
| Natural hydrolytic degradation of the sprayed film | 4–6 weeks | Not measurable | Up to 30 weeks |

The table clearly shows that, despite the same lactide/comonomer ratio, the three copolylactides have different properties and are thus different. Only the copolylactide according to the invention with a narrow molecular weight distribution, e.g., of below 2.0 (1.6 in this case) meets the preferred profile of requirements in terms of flexibility, transparency, adhesion and following of the contours of the skin. The copolymer according to EP 0509 203 has, owing to the low glass transition temperature of 22° C. and the low viscosity, a tacky consistency, which must lead to adhesion to textiles lying on top (for example dressing material). The viscosity of the copolymers according to the invention is usually between 0.30 and 0.75, preferably between 0.55 and 0.67. Hence they also differ from those in the two patent applications mentioned, which show either a higher or lower viscosity.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above or below, and of corresponding European application No. 99116119.1, filed Aug. 18, 1999, is hereby incorporated by reference.

All the characterization methods were carried out as follows:

DSC measurements in Al dishes under nitrogen with a heating rate of 20° C./min and the $T_g$ values from the $1^{st}$ heating plot listed.

Inherent viscosities at 250° C. with a polymer concentration of c=2 g/l in dichloromethane with automated Ubbelohde viscometer (from Lauda). GPC measurements in THF at 30° C. with poly(ε-caprolactone) calibration.

To purify the liquid initiator it was mixed with xylene (low-cost, nontoxic) or alternatively with toluene and distilled azeotropically twice. It was then fractionally distilled under high vacuum ($10^{-3}$ mbar), using the highest-boiling fraction as final product. All the tests described were carried out exclusively with purified initiator. This also applies to the comparative tests of the state of the art.

EXAMPLES

Example 1

(Lactide/ε-caprolactone 85:15, n-butanol 200:1)

24.5 g (170 mmol) of D,L-lactide (Boehringer S grade) and 3.42 g (30 mmol) of ε-caprolactone (distilled over $CaH_2$) were weighed into a 100 ml round-bottom flask, and a solution of 2 mg (0.005 mmol) of $SnOct_2$ (Aldrich, previously purified) and 74 mg (1 mmol) of n-butanol in 2 ml of dry diethyl ether was pipetted in. The flask with glass stopper in place was introduced into an oil bath heated to 160° C., the excess pressure was released by briefly opening, and the reactants were mixed by stirring with a magnetic stirrer. After 24 h, the temperature was lowered to 100° C. and, after a further 24 h, the test was cooled. It was then evacuated at 100° C. for 1 h. Measurements on the glassy crude product showed a glass transition temperature $T_g$=31° C., an inherent viscosity $\eta_{inh}$=0.40 dl/g, a molecular weight $M_n$=16,000 and $M_w$=24,000. The $M_n/M_w$ ratio derived therefrom is 1.5.

Example 2

(Lactide/ε-caprolactone 85:15, n-butanol 400:1)

24.5 g (170 mmol) of D,L-lactide (Boehringer S grade) and 3.42 g (30 mmol) of ε-caprolactone (distilled over $CaH_2$) were weighed into a 100 ml round-bottom flask, and a solution of 2 mg (0.005 mmol) of $SnOct_2$ and 37 mg (0.5 mmol) of n-butanol in 2 ml of dry diethyl ether was pipetted in. The reaction mixture was polymerized at 160° C. for 24 h and then at 100° C. for 24 h. The following values were found for the subsequently evacuated crude product: $T_g$=38° C.; $\eta_{inh}$=0.60 dl/g, $M_n$=30,000 and $M_w$=48,000. $M_n/M_w$=1.6.

Example 3

(Lactide/1,4-dioxan-2-one 85:15, triethylene glycol monomethyl ether 200:1)

24.5 g (170 mmol) of D,L-lactide and 3.06 g (30 mmol) of 1,4-dioxan-2-one (freshly distilled) were weighed into a 100 ml round-bottom flask, and a solution of 2 mg (0.005 mmol) of $SnOct_2$ and 164 mg (1 mmol) of triethylene glycol monomethyl ether in 2 ml of dry diethyl ether was added. The reaction mixture was polymerized as in Example 1. The following properties were measured for the evacuated crude product:

$T_g$=37° C.; $\eta_{inh}$=0.35 dl/g, $M_n$=15,000 and $M_w$=21,900. $M_n/M_w$=1.46.

Example 4

(Lactide/1,3-dioxan-2-one 85:15, n-butanol 400:1)

24.5 g (170 mmol) of D,L-lactide and 3.06 g (30 mmol) of 1,3-dioxan-2-one (trimethylene carbonate, Boehringer S grade) were weighed into 100 ml round-bottom flask, and a solution of 2 mg (0.005 mmol) of $SnOct_2$ and 37 mg (0.5 mmol) of n-butanol in 2 ml of dry diethyl ether was added. The reaction mixture was polymerized as in Example 1. The following properties were measured for the evacuated crude product:

$T_g$=40° C.; $\eta_{inh}$=0.68 dl/g, $M_n$=38,000 and $M_w$=55,000. $M_n/M_w$=1.4.

Example 5

(Lactide/ε-caprolactone 85:15, n-butanol 200:1)

A copolylactide is prepared in analogy to Example 1 with the exception that the polymerization was carried out in a single temperature step at 160° C. in a period of 36 h. Measurements on the glassy crude product showed a glass transition temperature $T_g=30°$ C., an inherent viscosity ηinh=0.38 dl/g, a molecular weight $M_n=18,000$ and $M_w=33,000$. The $M_w/M_n$ ratio derived therefrom is 1.8.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A flexible, transparent copolylactide comprising polymerized units of racemic lactide and a comonomer of ε-caprolactone, said copolylactide having a glass transition temperature of 33° to 37° C. and a polydispersity $P_n$ of 1.4 to 1.7, obtained by polymerizing racemic lactide with said ε-caprolactone comonomer at a temperature not exceeding 168° C., at a molar ratio of lactide to comonomer of 84:16, 85:15 or 86:14, in the presence of tin(II) di(ethylhexanoate) as an initiator, at a molar ratio of initiator to lactide/comonomer of 1:30,000 to 1:50,000, and in the presence of an n-alkanol cocatalyst, at a molar ratio of cocatalyst to lactide/comonomer of 1:200 to 1:600.

2. The copolylactide according to claim 1, wherein the cocatalyst is n-butanol.

3. The copolylactide according to claim 1, wherein the glass transition temperature of the copolylactide is 33 to 37° C.

4. The copolylactide according to claim 1, wherein the number average molecular weight $M_n$ is 25,000 to 40,000.

5. The copolylactide according to claim 1, wherein the polydispersity $P_n$ is 1.4 to 1.7.

6. A process for preparing a copolylactide, comprising polymerizing racemic lactide with an E-caprolactone comonomer, at a molar ratio of lactide to comonomer of 84:16, 85:15 or 86:14, in the presence of tin(II) di(ethylhexanoate) as an initiator, at a molar ratio of initiator to lactide/comonomer of 1:30,000 to 1:50,000, and in the presence of an n-alkanol cocatalyst, where the molar ratio of cocatalyst to lactide/comonomer is 1:200 to 1:600, at a temperature not exceeding 165° C.

7. The process according to claim 6, wherein the polymerization is carried out at a temperature of from 155 to 165° C. for 20 to 28 h and then at a temperature of 90 to 120° C. for a further 20 to 28 h.

8. The process according to claim 6, wherein the molar ratio of initiator to lactide/comonomer is about 1:40,000 and the molar ratio of cocatalyst to lactide/comonomer is 1:300 to 1:500.

9. The process according to claim 6, further comprising subjecting a polymerized product to a vacuum treatment.

10. A flexible, transparent copolylactide obtained by a process according to claim 6.

11. A copolylactide according to claim 1, additionally comprising a plasticizer.

12. A process for controlling the molecular weight distribution $M_w/M_n$ of a copolymer comprising polymerized units of racemic lactide and at least one comonomer of ε-caprolactone, comprising polymerizing racemic lactide with an ε-caprolactone comonomer, at a molar ratio of lactide to comonomer of 84:16, 85:15 or 86:14, in the presence of tin(II) di(ethylhexanoate) as an initiator, at a molar ratio of initiator to lactide/comonomer of 1:30,000 to 1:50,000, and in the presence of an n-alkanol cocatalyst, where the molar ratio of cocatalyst to lactide/comonomer is 1:200 to 1:600, at a temperature not exceeding 165° C., whereby $M_w/M_n$ is 1.2 to 2.0.

13. The copolylactide according to claim 1, further comprising a solvent.

14. The copolylactide according to claim 13, further comprising a disinfectant and/or an anaesthetic.

15. The process according to claim 6, further comprising producing a surgical operation film, wound coverings or liquid gloves from said copolylactide.

16. A sunscreen, surgical operation film, wound absorbable adhesive covering or liquid glove, comprising a copolylactide according to claim 1.

17. A flexible, transparent copolylactide comprising polymerized units of racemic lactide and a comonomer of ε-caprolactone, δ-valerolactone, 1,4dioxan-2-one, 1,3-dioxane-2-one or mixtures thereof, having a glass transition temperature of 33 to 37° C., a number average molecular weight $M_n$ of 15,000 to 50,000 and a polydispersity $P_n$ of 1.4 to 1.7.

18. A process for preparing a copolylactide, comprising polymerizing racemic lactide with an ε-caprolactone, δ-valerolactone, 1,4-dioxan-2-one or 1,3-dioxan-2-one comonomer, or a mixture thereof, at a molar ratio of lactide to comonomer of 90–80:10–20, in the presence of tin(II) di(ethylhexanoate) as an initiator, at a molar ratio of initiator to lactide/comonomer of 1:30,000 to 1:50,000, and in the presence of an n-alkanol, an oligoethylene glycol monomethyl ether or a polyol cocatalyst, where the molar ratio of cocatalyst to lactide/comonomer is 1:200 to 1:600, at a temperature not exceeding 165° C.

19. A process for controlling the molecular weight distribution $M_w/M_n$ of a copolymer comprising polymerized units of racemic lactide and at least one comonomer of ε-caprolactone, δ-valerolactone, 1,4-dioxan-2-one, 1,3-dioxan-2-one or a mixture thereof, comprising polymerizing racemic lactide with an ε-caprolactone, δ-valerolactone, 1,4-dioxan-2-one or 1,3-dioxan-2-one, comonomer, or a mixture thereof, at a molar ratio of lactide to comonomer of 90–80:10–20, in the presence of tin(II) di(ethylhexanoate) as an initiator, at a molar ratio of initiator to lactide/comonomer of 1:30,000 to 1:50,000, and in the presence of an n-alkanol, an oligoethylene glycol monomethyl ether or a polyol cocatalyst, where the molar ratio of cocatalyst to lactide/comonomer is 1:200 to 1:600, at a temperature not exceeding 165° C., whereby $M_w/M_n$ is 1.2 to 2.0.

20. A flexible, transparent copolylactide according to claim 1, wherein the polydispersity $P_n$ is 1.4 to 1.7.

21. A flexible, transparent copolylactide comprising polymerized units of racemic lactide and a comonomer of 1,4-dioxan-2-one, 1,3-dioxane-2-one or mixtures thereof, having a glass transition temperature of 30 to 43° C., a number average molecular weight $M_n$ of 15,000 to 50,000 and a polydispersity $P_n$ of 1.2 to 2.0.

22. A process for preparing a copolylactide, comprising polymerizing racemic lactide with an 1,4-dioxan-2-one or 1,3-dioxan-2-one comonomer, or a mixture thereof, at a molar ratio of lactide to comonomer of 90–80:10–20, in the presence of tin(II) di(ethylhexanoate) as an initiator, at a molar ratio of initiator to lactide/comonomer of 1:30,000 to 1:50,000, and in the presence of an n-alkanol, an oligoethylene glycol monomethyl ether or a polyol cocatalyst, where the molar ratio of cocatalyst to lactide/comonomer is 1:200 to 1:600, at a temperature not exceeding 165° C.

23. A process for controlling the molecular weight distribution $M_w/M_n$ of a copolymer comprising polymerized units of racemic lactide and at least one comonomer of 1,4-dioxan-2-one, 1,3-dioxan-2-one or a mixture thereof, comprising polymerizing racemic lactide with an ε-caprolactone, δ-valerolactone, 1,4-dioxan-2-one or 1,3-dioxan-2-one, comonomer, or a mixture thereof, at a molar ratio of lactide to comonomer of 90–80:10–20, in the presence of tin(II) di(ethylhexanoate) as an initiator, at a molar ratio of initiator to lactide/comonomer of 1:30,000 to 1:50,000, and in the presence of an n-alkanol, an oligoethylene glycol monomethyl ether or a polyol cocatalyst, where the molar ratio of cocatalyst to lactide/comonomer is 1:200 to 1:600, at a temperature not exceeding 165° C., whereby $M_w/M_n$ is 1.2 to 2.0.

* * * * *

UNITED STATES PATENT AND TRADEMARK OFFICE
CERTIFICATE OF CORRECTION

PATENT NO.    : 6,472,502 B1
DATED         : October 29, 2002
INVENTOR(S)   : Jurgens et al.

It is certified that error appears in the above-identified patent and that said Letters Patent is hereby corrected as shown below:

Column 8,
Line 22, change "4dioxan" to -- 4-dioxan --.

Signed and Sealed this

Tenth Day of June, 2003

JAMES E. ROGAN
*Director of the United States Patent and Trademark Office*